United States Patent [19]

Goto et al.

[11] 4,115,355

[45] Sep. 19, 1978

[54] NOVEL DERIVATIVES USEFUL AS ADDITIVES FOR INHIBITING THE DETERIORATION OF DEGRADABLE SUBSTANCES

[75] Inventors: Kuniaki Goto, Tokyo; Kazumi Kodama, Yokohama, both of Japan

[73] Assignee: Nippon Zeon Co. Ltd., Tokyo, Japan

[21] Appl. No.: 748,648

[22] Filed: Dec. 8, 1976

[30] Foreign Application Priority Data

Dec. 18, 1975 [JP] Japan ................ 50-151078

[51] Int. Cl.$^2$ .................. C07C 39/16; C01M 1/54
[52] U.S. Cl. .................. 260/45.95 H; 208/18; 252/404; 260/814; 568/721
[58] Field of Search ........... 260/619 A, 619 D, 45.95, 260/814; 208/18; 252/404

[56] References Cited

U.S. PATENT DOCUMENTS

| | | | |
|---|---|---|---|
| 2,732,407 | 1/1956 | Lambert et al. | 260/619 A |
| 2,976,260 | 3/1961 | Newland et al. | 260/619 A |
| 3,491,157 | 1/1970 | Dretzler et al. | 260/619 A |
| 3,544,512 | 12/1970 | Dretzler et al. | 260/619 A |
| 4,008,284 | 2/1977 | Goto et al. | 260/619 D |
| 4,066,562 | 1/1978 | Wollensak et al. | 260/619 A |

*Primary Examiner*—Norman Morgenstern
*Attorney, Agent, or Firm*—Sherman & Shalloway

[57] ABSTRACT

A phenol derivative of the general formula

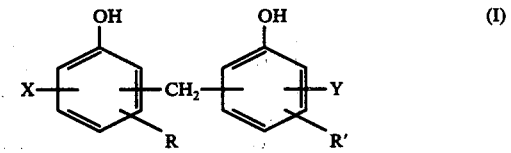

wherein R and R' are a hydrogen atom or an alkyl group containing 1 to 4 carbon atoms, and X and Y, which may be identical or different, each represent a cyclopentyl or cyclohexyl group. The above phenol derivatives are useful as additives for inhibiting the deterioration of various degradable substances such as polymeric substances, or oily substances.

8 Claims, No Drawings

NOVEL DERIVATIVES USEFUL AS ADDITIVES FOR INHIBITING THE DETERIORATION OF DEGRADABLE SUBSTANCES

This invention relates to novel phenol derivatives, and more specifically, to novel phenol derivatives useful as additives for inhibiting the deterioration of various degradable substances such as polymeric substances (e.g., plastics or rubbers), or oily substances (e.g., lubricating oils or heat transfer media).

Generally, polymeric substances such as plastic or rubbers degraded by the action of oxygen, ozone, or light during processing or storage whereby they are colored, become opaque, and undergo surface cracking or deterioration in physical properties such as tensile strength. In order to prevent such undesirable degradation, various agents for inhibiting degradation have been developed. In particular, amino compounds, phenol compounds, sulfide compounds and phosphite compounds are generally used as anti-oxidants. The amine compounds have superior property of inhibiting degradation, but since they are susceptible to staining, they cannot be used in those fields which must avoid coloration. In these fields, therefore, the phenolic compounds or sulfide compounds such as 2,6-ditertiary butyl-p-cresol, 2,2'-methylene bis(4-methyl-6-tertiary butylphenol) or 4,4-thiobis(6-tertiary butyl-3-methylphenol) are usually employed as anit-oxidants. These compounds, however, do not possess sufficient ability to inhibit degradation, and suffer from the defect that when polymeric substances containing these compounds are exposed to heat for long periods of time, they are either colored or gelled.

In the present application, the terms "degradation" and "deterioration" are used interchangeably.

It is an object of this invention to provide novel compounds which possess better ability to inhibit degradation than the conventional phenolic anti-oxidants, and are not susceptible to staining.

Another object of this invention is to provide a novel anti-degradative agent comprising the above compound as an active ingredient.

Other objects of this invention will become apparent from the following description.

We have found that phenol derivatives of the general formula

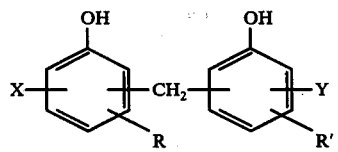 (I)

wherein R and R' are a hydrogen atom or an alkyl group containing 1 to 4 carbon atoms, and X and Y, which may be identical or different, each represent a cyclopentyl or cyclohexyl group, meet these objects.

Specific examples of the phenol derivatives of general formula [I] are 2,2'-methylene bis(6-cyclopentylphenol), 2,2'-methylene bis(4-cyclopentylphenol), 2,2'-methylene bis(4-methyl-6-cyclopentylphenol), 2,2'-methylene bis(4-methyl-6-cyclohexylphenol), 2,2'-methylene bis(4-ethyl-6-cyclopentylphenol), 2,2'-methylene bis(4-methyl-6-cyclopentylphenol), 2,2'-methylene bis(4-cyclopentyl-6-methylphenol), 2,2'-methylene bis(4-cyclohexyl-6-methylphenol) and 2,2'-methylene bis(4-cyclopentyl-6-butylphenol).

Degradation of degradative substances can be effectively inhibited by adding one or more of these phenol derivatives in an amount of 0.005 to 5 parts, preferably 0.01 to 2 parts by weight per 100 parts by weight of the degradable substances. For example, when the degradable substance is a natural or synthetic rubber, gel formation ascribable to oxygen and/or heat can be inhibited. When the degradable substance is a plastic article, such as polyethylene or polypropylene, an oily product such as a lubricating oil or heat transfer medium, its degradation by oxygen and/or light can be inhibited.

Among the phenol derivatives expressed by formula [I], compounds in which R and R' are both methyl groups, i.e., cresol derivatives, especially p-cresol, possess the ability to inhibit degradation. In general, among the phenol derivatives of formula [I], compounds in which X and Y are both cyclopentyl groups, particularly, compounds having cyclopentyl groups adjacent to the OH group, have especially superior properties. Also, the phenol derivatives of formula [I] should preferably be those in which the methylene bond between the two benzene nuclei exits via carbon atoms that are each adjacent to a carbon atom having the OH group. That is, the phenol derivatives of formula [I] should preferably have a 2,2'-type methylene bond.

Procedures of adding the phenol derivatives to degradable substances and their amounts to be added are the same as those employed in the prior art, and if desired, known anti-oxidants, ultraviolet absorbers, and color inhibitors, etc. can also be used together with these phenol derivatives.

The phenol derivatives of formula [I] can be easily prepared by reacting at least one of a compound of the following formula

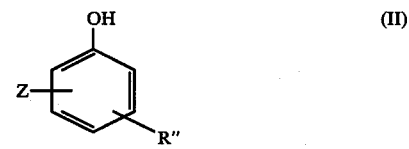 (II)

wherein R" is a hydrogen atom or an alkyl group containing 1 to 4 carbon atoms, and Z represents a cyclopentyl or cyclohexyl group,
with formaldehyde in the presence of an acid catalyst such as hydrochloric acid, sulfuric acid or boron trifluoride. The reaction usually ends in 0.5 to 100 hours at 0° to 200° C. Since the reaction is performed stoichiometrically, about 0.5 mole of formaldehyde is ordinarily used per mole of the compound of formula [II]. In some cases, about 0.2 to 2 moles of formaldehyde can be used per mol of the compound of formula [II].

Preferred species of the compound of formula [II] are those in which cyclopentyl or cyclohexyl and hydrogen, methyl, ethyl, propyl or butyl are bonded at the ortho-, meta- or para-position to the hydroxyl group. Specific examples include 2-cyclopentyl phenol, 2-cyclohexyl phenol, 2-methyl-6-cyclopentyl phenol, 2-methyl-6-cyclohexyl phenol, 3-methyl-6-cyclopentyl phenol, 2-cyclopentyl-4-methyl phenol, 2-cyclohexyl-4-methyl phenol, 2-cyclopentyl-4-ethyl phenol, and 2-cyclopentyl-4-butyl phenol.

The phenol derivatives of this invention differ from the conventional anti-oxidants in that two cycloaliphatic groups (X and Y) are contained. Because of this, they have very good ability to inhibit degradation. For example, the phenol derivatives of this invention have far superior ability to inhibit degradation then 2,6-ditertiary butyl-p-cresol which has been widely used as an anti-oxidant, and better ability to inhibit degradation than 2,2-methylene bis(4-methyl-6-tertiary butyl phenol) which has similar structure to the phenol derivatives.

The phenol derivatives of this invention can find utility not only as agents for inhibiting deterioration, especially anti-oxidants, but also as polymerization inhibitors.

less steel gauze, and immersing the cage in 100 ml of toluene for 24 hours to examine the amount of gel remaining in the cage. Coloration of the rubbers after the treatment of heat deterioration was also examined.

Also, as controls, 2,6-ditertiary-butyl-4-methyl phenol (BHT) that is usually used as a phenolic-type deterioration inhibitor and 2,2'-methylene-bis(4-methyl-6-tertiary-butyl phenol) (MMT) having a structure resembling that of the additive for inhibiting the deterioration of the present invention, were measured for their properties in the same manner as that of the present invention. The results were as shown in Table 1.

Table 1

| Heating time (at 100° C.) | Amount added (% by wt.) | Present invention MMC | Control BHT | MMT | No addition |
|---|---|---|---|---|---|
| 6 Hours | 0.02 | 6.5% (Pale yellow) | Not measured | 12.5% (Yellow) | 45% (Yellow) |
|  | 0.1 | 4.0 (Yellow) | 42.0 (Yellow) | 6.0 (Brown) |  |
|  | 0.5 | 1.5 (Pale brown) | 5.0 (Dense yellow) | 3.0 (Reddish yellow) |  |
| 16 Hours | 0.02 | 15 (Yellow) | Not measured | 26.0 (Dense yellow) | 66 (Pale brown) |
|  | 0.1 | 9.5 (Yellow) | 71.0 (Pale brown) | 18.0 (Reddish brown) |  |
|  | 0.5 | 8.0 (Brown) | 40.0 (Pale brown) | 15.0 (Dense reddish brown) |  |

The following non-limitative Examples specifically illustrate the present invention. In all of the Examples, the parts indicated are by weight.

EXAMPLE 1

To a 500 ml flask were introduced 87 g of 2-cyclopentyl-4-methylphenol and 25.5 g of para-formaldehyde that was dissolved in 80 ml of ethanol, followed by the addition of a solution of 4 g of dry hydrogen chloride in 20 ml of ethanol at 70° C. over a period of 10 minutes. Thereafter, the reaction was conducted at 70° C. for 48 hours with stirring. The reaction solvent was then distilled off, and the precipitated white substance was taken by filtration, and washed with water and further with n-heptane.

The so obtained white crystalline compound exhibited a melting point of 104.4° C.

The infrared-ray absorption specturm of the compound showed an absorption at 3480 $cm^{-1}$ indicating the presence of hydroxyl groups, and showed absorption near 1740 $cm^{-1}$ and 860 $cm^{-1}$ indicating that the compound is a 1,2,3,5-nuclear-substituted product. Analysis of the compound by nuclear magnetic resonance spectrum showed that it is 2,2'-methylene-bis(4-methyl-6-cyclopentyl phenol).

EXAMPLE 2

0.02 Part by weight, 0.1 part by weight and 0.5 part by weight of the 2,2'-methylene-bis(4-methyl-6-cyclopentyl phenol) (MMC) obtained in Example 1 were each added as an additive for inhibiting deterioration, to 100 parts by weight of a styrene-butadiene rubber (combined styrene 23.5%) that had been masticated beforehand with a three-inch roll. The mixtures were each kneaded several times to obtain test rubbers. The test rubbers were subjected to a treatment of heat deterioration by leaving them in a Geer's oven heated at 100° C. for certain periods of time (6 hours and 16 hours), and the gel content of each of the specimens was measured. Measurement of the gel content was performed by placing 0.2 g of a rubber in a cage made of a 80-mesh stainless steel gauze, and immersing the cage in 100 ml of toluene for 24 hours to examine the amount of gel remaining in the cage.

The styrene-butadiene rubbers to which was added the additive for inhibiting deterioration of the present invention formed the gel in small amounts even after they were left to stand in the Geer's oven heated at 100° C. for 16 hours. The gel, on the other hand, was formed in large amounts by the rubbers to which was added 2,6-ditertiary-butyl-4-methyl phenol (that has been widely recommended as a non-staining deterioration inhibitor) after the rubbers were deteriorated by the heat treatment for 6 hours. The 2,2'-methylene-bis(4-methyl-6-tertiary-butyl phenol) having a structure similar to the deterioration inhibitor of the present invention exhibits better properties than BHT but forms a gel in larger amounts than the deterioration inhibitor of the present invention.

As for the coloration after the heat deterioration treatment, the MMT developed coloration markedly, whereas the additive for inhibiting the deterioration of the present invention developed coloration to a degree nearly equal to that of BHT. From these results, it is seen that the additive for inhibiting the deterioration of the present invention gives excellent properties for preventing rubbers from being deteriorated.

EXAMPLE 3

The 2,2'-methylene-bis(4-methyl-6-cyclopentyl phenol) obtained in Example 1 was added in an amount of 0.3% by weight to 100 parts by weight of high-density polyethylene (density 0.957 $g/cm^3$, melt index 0.8 g/10 min.), and each of the mixtures was then kneaded with a roll. The kneading was performed at 155° C. for the polyethylene, and at 170° C. for the polypropylene. After the kneading, the mixtures were each formed into a sheet of a thickness of 0.3 mm by means of a press, and cut into pieces of a size of 40 mm × 100 mm. The so obtained samples were then measured for their oxygen absorption amount at 150° C. in order to examine the time required for 1 g of the resin to absorb 2 cc of oxygen. The results were as shown in Table 2 below.

Table 2

| Resin | Additive for inhibiting deterioration | |
|---|---|---|
| | MMC | BHT |
| Polyethylene | 350 min. | 200 min. |
| Polypropylene | 520 min. | 190 min. |

The above results indicate that the additive for inhibiting the deterioration of the present invention gives superior effects of preventing the deterioration of plastics such as polyethylene and polypropylene.

What we claim is:

1. A stabilized composition of a degradable oily or polymeric substance comprising an oily or polymeric degradable substance and an amount effective for inhibiting the deterioration of the degradable substance of 2,2'-methylene-bis(4-methyl-cyclopentyl phenol) as an active ingredient.

2. The composition of claim 1 wherein the active ingredient is 2,2'-methylene bis(4-methyl-6-cyclopentyl phenol).

3. The composition of claim 1 wherein the amount of the active ingredient is from 0.005 to 5 parts by weight per 100 parts by weight of the degradable substance.

4. The composition of claim 1 wherein the amount of the active ingredient is from 0.01 to 2 parts by weight per 100 parts by weight of the degradable substance.

5. The composition of claim 2 wherein the amount of the active ingredient is from 0.005 to 5 parts by weight per 100 parts by weight of the degradable substance.

6. The composition of claim 2 wherein the amount of the active ingredient is from 0.01 to 2 parts by weight per 100 parts by weight of the degradable substance.

7. 2,2'-Methylene-bis(4-methyl-cyclopentyl phenol).

8. 2,2'-Methylene-bis(4-methyl-6-cyclopentyl phenol).

* * * * *